US011413363B2

(12) United States Patent
Cruz (10) Patent No.: US 11,413,363 B2
(45) Date of Patent: Aug. 16, 2022

(54) CHARGING AND SANITATION SYSTEM CONVERSION KIT

(71) Applicant: Jesus Cruz, Miami, FL (US)

(72) Inventor: Jesus Cruz, Miami, FL (US)

( * ) Notice: Subject to any disclaimer, the term of this patent is extended or adjusted under 35 U.S.C. 154(b) by 315 days.

(21) Appl. No.: 16/855,383

(22) Filed: Apr. 22, 2020

(65) Prior Publication Data

US 2021/0052755 A1 Feb. 25, 2021

Related U.S. Application Data

(60) Provisional application No. 62/922,591, filed on Aug. 19, 2019.

(51) Int. Cl.
*A61L 2/10* (2006.01)
*H02J 7/00* (2006.01)
*A61L 2/26* (2006.01)

(52) U.S. Cl.
CPC ............. *A61L 2/10* (2013.01); *A61L 2/26* (2013.01); *H02J 7/0044* (2013.01); *A61L 2202/11* (2013.01); *A61L 2202/122* (2013.01); *A61L 2202/14* (2013.01)

(58) Field of Classification Search
CPC .......... A61L 2/10; A61L 2/26; A61L 2202/11; A61L 2202/122; A61L 2202/14; A61L 2/00; A61L 2/02; A61L 2/08; H02J 7/0044

See application file for complete search history.

(56) References Cited

U.S. PATENT DOCUMENTS

| | | | |
|---|---|---|---|
| 6,813,848 B2 * | 11/2004 | Ortamala | E01H 5/066 37/273 |
| 7,130,190 B1 | 10/2006 | Baker | |
| 8,597,588 B1 * | 12/2013 | Trabalka | A61L 2/10 250/455.11 |
| 9,968,697 B1 | 5/2018 | Philipps | |
| 10,328,166 B2 * | 6/2019 | Georgeson | B08B 5/02 |
| 10,376,604 B2 | 6/2019 | Romo et al. | |
| 10,476,285 B2 | 11/2019 | Ergun et al. | |
| 2010/0193709 A1 * | 8/2010 | Dalton | A61L 2/10 250/504 R |
| 2013/0175993 A1 | 7/2013 | Chen | |
| 2017/0165386 A1 * | 6/2017 | Huang | A61L 2/26 |

* cited by examiner

*Primary Examiner* — Bao Q Truong
(74) *Attorney, Agent, or Firm* — Joel Douglas; Thomas Ciesco (57) ABSTRACT

The invention relates to systems, devices, and methods for storing, charging, sterilizing, transporting and networking mobile computing devices, such as tablet computing devices, phones, virtual reality headsets and, more particularly to a kit for modifying an existing charging cabinet to provide ultraviolet light to sterilize the tablet computing devices, phones, virtual reality headsets.

10 Claims, 12 Drawing Sheets

CHARGING AND SANITATION SYSTEM CONVERSION KIT

CROSS-REFERENCE TO RELATED APPLICATION

This application claims priority from U.S. Provisional Patent Application No. 62/922,591, filed Aug. 19, 2019, titled All in one ultraviolet sterilization of virtual reality headsets, tablets, smart phones, and electronic devices which is hereby incorporated by reference herein for all purposes.

Trademarks used in the disclosure of the invention and the applicants make no claim to any trademarks referenced.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

1) Field of the Invention

Current state of the art is that companies, hospitals, government agencies utilize tablet PCs and Virtual Reality headsets charging carts which are used to charge and safely store the tablet PCs and Virtual Reality headsets. With the advent of the need to prevent the spread of diseases and the increased need for providing shared use devices which do not present a possibility of spreading bacterial or viral based diseases there is a need to provide a method to charge and sanitize tablet PCs and Virtual Reality headsets.

This disclosure generally relates to systems, devices, and methods for storing, charging, sterilizing, transporting and networking mobile computing devices, such as tablet computing devices, phones, virtual reality headsets and, more particularly to a kit for modifying an existing charging cabinet to provide ultraviolet light to sterilize the tablet computing devices, phones, virtual reality headsets.

2) Description of Related Art

Currently companies, hospitals government agencies utilize tablet PCs and Virtual Reality headsets charging carts however these carts do not have the ability to sterilize the tablet PCs and Virtual Reality headsets which are stored in the charging cart. These tablet PCs and Virtual Reality headsets are a shared device and are utilized by more than one patient or client.

Therefore, what is needed in the art is a kit for modifying a cart for storing and charging tablet PCs and Virtual Reality headsets. Specifically, a tablet ad storage and Virtual Reality headsets charging cart, which uses tablet cradles and Virtual Reality headsets cradles for storing and charging the tablets and Virtual Reality headsets in a cabinet. The kit modifies the cart for storing and charging tablet PCs and Virtual Reality headsets to provide cradles, Ultraviolet lights and a control system to sterilize and charge the tablet PCs and Virtual Reality headsets.

BRIEF SUMMARY OF THE INVENTION

The invention in one form is directed to a conversion kit for modifying a virtual reality headset and tablet charging cabinet to incorporate ultraviolet sterilization as well as charging maintain the ability to charge the virtual reality headset and tablets.

The invention provides the user a modification kit to modify a charging cabinet for tablets and virtual reality head sets and add ultraviolet light (UV) light and brackets, templates and install UV lights so that each tablets and virtual reality head set receives the proper dosage of UV light to sterilize each tablet and virtual reality head set.

An advantage of the present invention is that the tablets and virtual reality headsets when the cabinet is converted are charged and sterilized to eliminated the threat of contaminating anther user/patient or client of the head set or tablet with a virus or bacterial infection.

BRIEF DESCRIPTION OF THE DRAWINGS

A further understanding of the nature and advantages of particular embodiments may be realized by reference to the remaining portions of the specification and the drawings, in which like reference numerals are used to refer to similar components. When reference is made to a reference numeral without specification to an existing sub-label, it is intended to refer to all such multiple similar components.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Currently in the prior art is replete with charging and storage systems such as those described in U.S. Pat. No. 9,968,697 issued to Philipps, U.S. Pat. No. 10,476,285 issued to Ergun, U.S. Pat. No. 7,130,190 issued to Baker, U.S. Pat. No. 10,376,604 issued to Romo, et al., U.S. Pat. No. 10,328,166 issued to Georgeson, U.S. Patent application 20130175993 invented by Chen which are hereby incorporated by reference herein for all purposes.

Embodiments described herein provide a system and method for the modification of a charging device which provides the charging device the capability and methods for to sterilizing or sanitizing and/or storing and/or transporting and/or charging and/or networking one or more tablet computing devices and virtual reality headsets. As discussed above, tablet computing devices and virtual reality headsets are well known and are also referred to herein as tablets and headsets. In general, a tablet is a mobile computer, typically integrated into a flat touch screen and primarily operated by touching the screen, often including an onscreen virtual keyboard, rather than using a physical keyboard and a virtual reality head set (headset) is a head-worn apparatus that completely covers the eyes for an immersive 3D experience. The form factor of a tablet offers a more mobile way to interact with a computer. The fact that the headset is worn on the face and proximal to the user's eyes, nose, mouth and ears is a concern when the headset is used by different users or shared. The proximity to the user's eyes, nose, mouth and ears when a headset is not properly sanitized can result in pink eye, viral infections such as colds and flu infections. Specifically, as used in this disclosure the flu is a contagious respiratory illness caused by influenza viruses that infect the nose, throat, and sometimes the lungs. Typically, headsets and tablets have a battery that needs to be periodically charged, software that may need to be periodically updated or maintained, and data that may need to be backed up from, or transferred to the tablet or headset as well as sterilizing the tablet.

Currently many facilities that utilize tablets and headsets as a shared resource already have charging and storage cabinets for the tablets and headsets. However, as these systems become more prevalent the need to provide increase sanitization capability above and beyond wiping the tablets and headsets with sanitizing wipes is needed.

The invention utilizes Ultraviolet light (UV) light which is electromagnetic radiation with wavelengths shorter than visible light but longer than X-rays. UV can be separated into various ranges, with short-wavelength UV (UVC) considered "germicidal UV". Wavelengths between about 200 nm and 300 nm are strongly absorbed by nucleic acids. The absorbed energy can result in defects including pyrimidine dimers. These dimers can prevent replication or can prevent the expression of necessary proteins, resulting in the death or inactivation of the organism.

Mercury-based lamps operating at low vapor pressure emit UV light at the 253.7 nm line. Ultraviolet light-emitting diodes (UV-C LED) lamps emit UV light at selectable wavelengths between 255 and 280 nm.

Pulsed-xenon lamps emit UV light across the entire UV spectrum with a peak emission near 230 nm.

UVC LED devices can also be use with wavelengths between wavelengths between 255 and 280 nm.

This process is similar to the effect of longer wavelengths (UVB) producing sunburn in humans. Microorganisms have less protection against UV, and cannot survive prolonged exposure to it.

A UV system is designed to expose environments to germicidal UV. Exposure comes from germicidal lamps that emit germicidal UV at the correct wavelength, thus irradiating the environment. The forced flow of air or water through this environment ensures exposure.

One issue with UV lights is that they are susceptible to dust and dust accumulation can reduce their effectiveness.

The present invention relates to a kit for modifying a cart for storing and charging tablet PCs and Virtual Reality headsets. Specifically, a tablet ad storage and Virtual Reality headsets charging cart, which uses tablet cradles and Virtual Reality headsets cradles for storing and charging the tablets and Virtual Reality headsets in a cabinet. The kit modifies the cart for storing and charging tablet PCs and Virtual Reality headsets to provide cradles, Ultraviolet lights and a control system to sterilize and charge the tablet PCs and Virtual Reality headsets.

As used in this specification the terms UV lights, UVC lights, UV Led's, UVC Led are meant to mean Ultraviolet light (UV) light which is electromagnetic radiation with wavelengths shorter than visible light but longer than X-rays and more particularly light producing mechanisms with wavelengths between 220 and 300 nm.

As used in this specification the terms smart phones or tablet computers are used interchangeably.

As used in this specification the terms box, cart, caddy and cabinet are used interchangeably to mean a cart with charging and sterilization stations.

Figure 1:
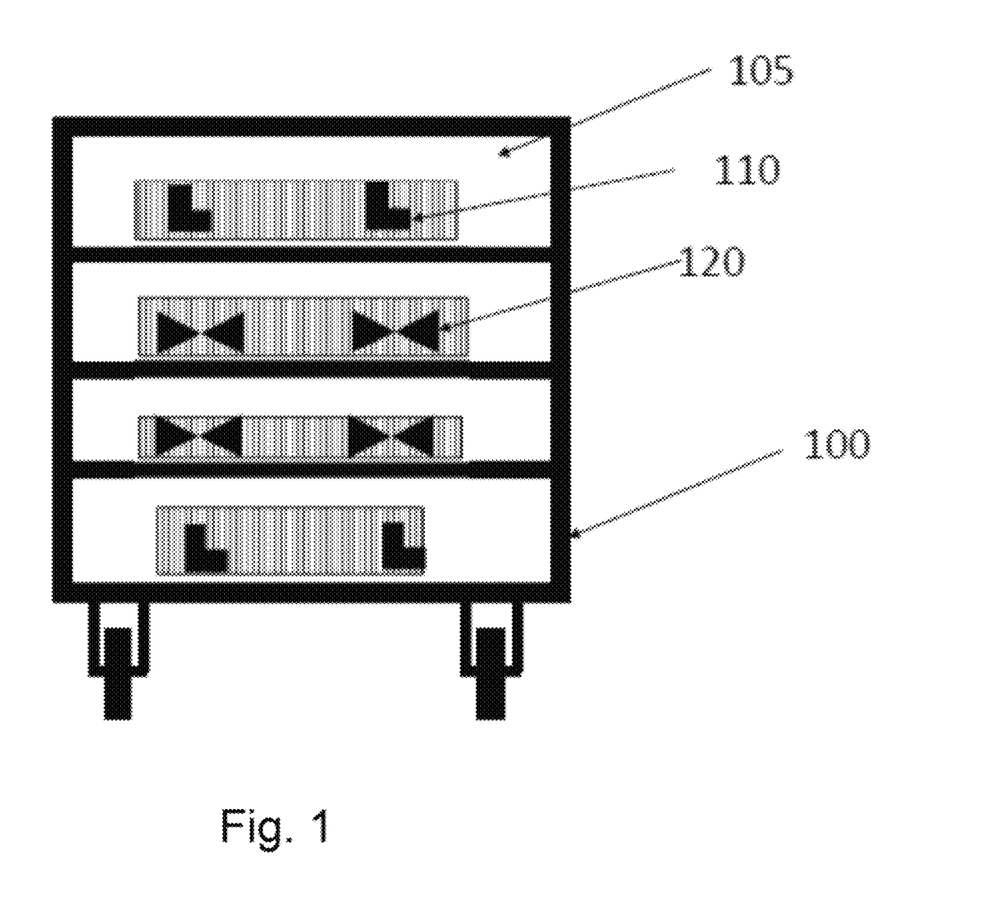
FIG. 1, shows a front view of a typical charging and storage cart for tablets and headsets.

Referring now to the drawings FIG. 1-FIG. 12, and more particularly to FIG. 1, there is shown a typical charging and storage cart for tablets and headsets. Some embodiments provide a tablet storage device in the form of a tablet storage cart 100 for storing, transporting, charging, and/or networking one or more tablets. Tablet storage carts 100 and other tablet storage devices, can be provided with various physical configurations and features and may not provide adequate storage and charging support for virtual reality headsets. The typical configuration has draws 105 with tablet cradles 110 and headset cradles 120 for storing the tablets and the headsets. However, there is no accommodation for sterilization of the tablets and the headsets.

Figure 2:
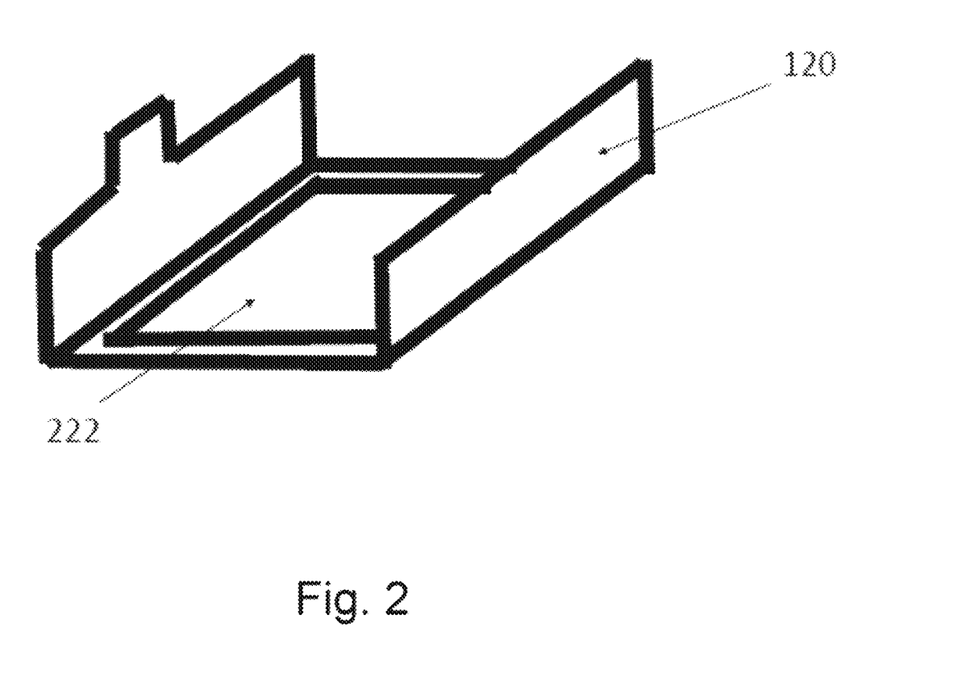
FIG. 2, shows one embodiment of a headset cradle.

Referring to FIG. 2, there is shown one embodiment of a headset cradle 120 of the of the invention. The headset cradle 120 is designed to hold and charge the head set. The headset cradle 120 holds the headset such that the portions of headset that are in contact with the user are facing up. The cradle also allows light to bath the head set from below and above due to the large opening 222. The headset cradle 120 can be configured to charge the headset through a cord and connector or through capacitive charging depending on the particular specification of the headset.

Figure 3:
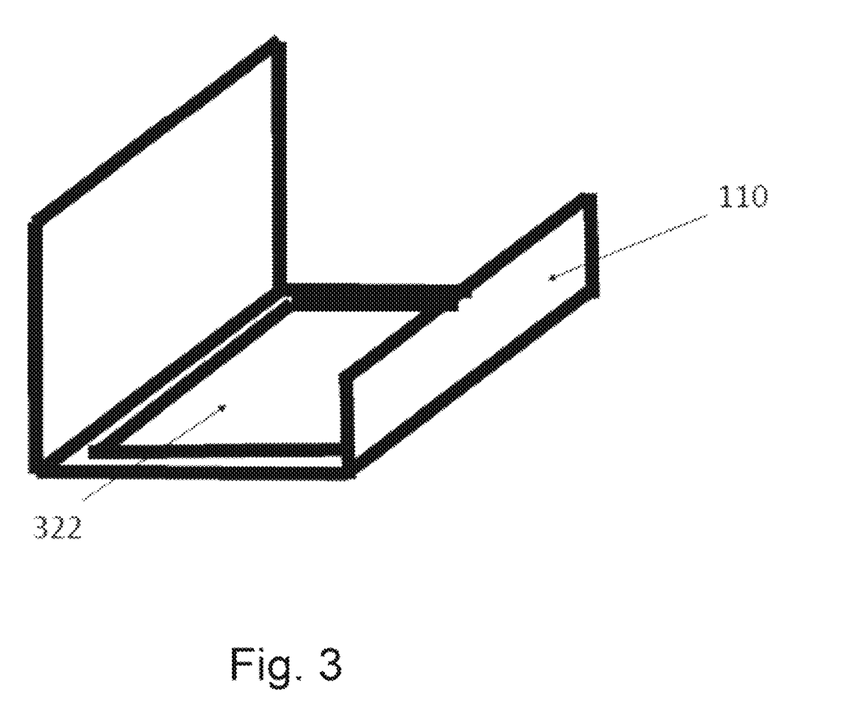
FIG. 3, shows one embodiment of a tablet cradles.

Referring to FIG. 3, there is shown one embodiment of a tablet cradles 110 of the of the invention. The tablet cradles 110 is designed to hold and charge the head set. The tablet cradles 110 holds the tablet such that the portions of tablet that are in contact with the user are facing up. The cradle also allows light to bath the tablet from below and above due to the large opening 322. The tablet cradles 110 can be configured to charge the headset through a cord and connector or through capacitive charging depending on the particular specification of the headset. The cradle can be used for either smart phones or tablet computers.

Figure 6:
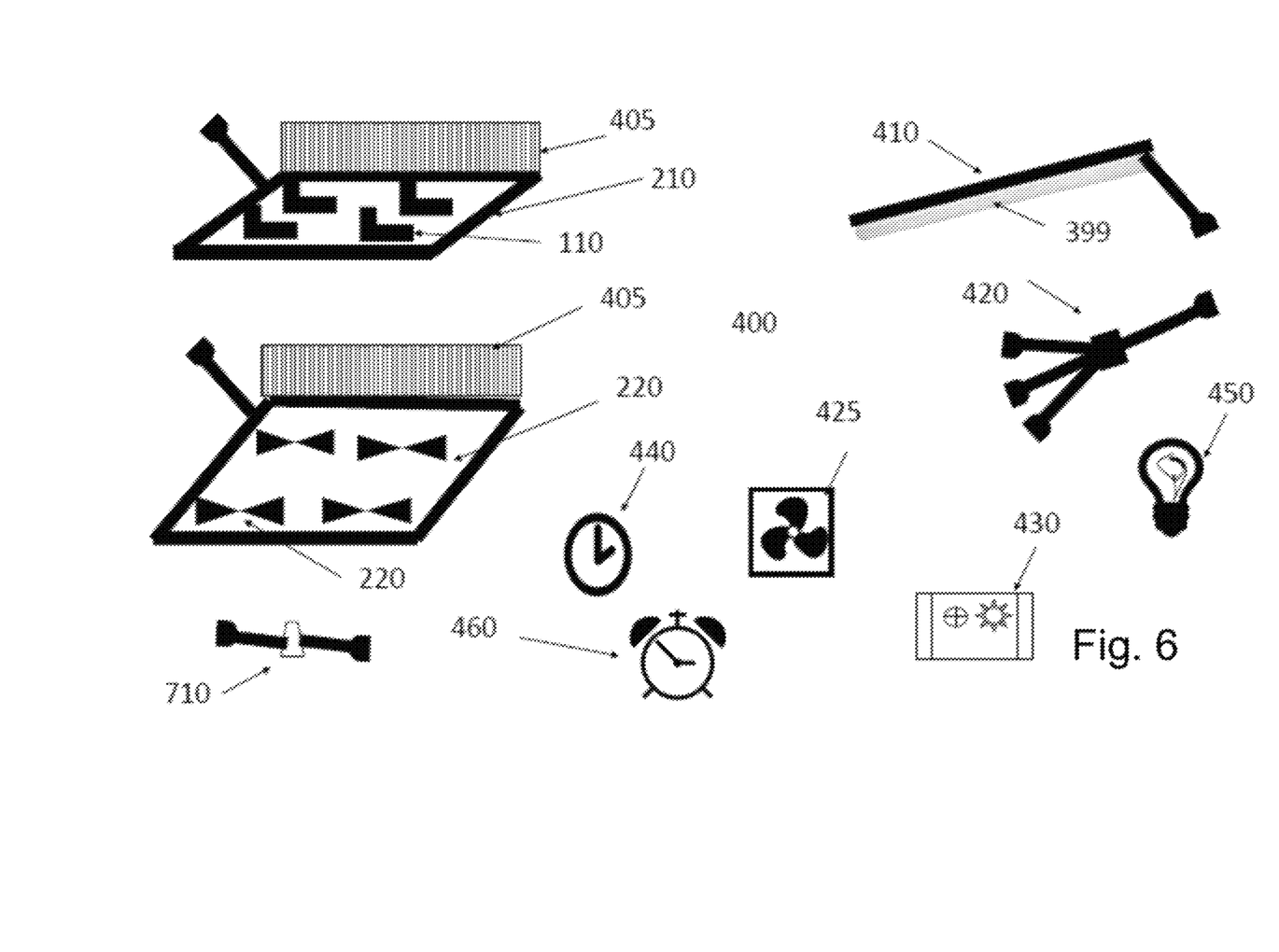
FIG. 6 shows one embodiment of the kit.

Referring to FIG. 6, there is shown one embodiment of the kit 400 of the present invention. The kit has all the components that a user would need to convert a tablet storage cart 100 for charging and storage of tablets and tablets and headsets into a tablet and headset storage cart 200 for sanitizing, charging and storage of tablets, phones and headsets.

Figure 4:
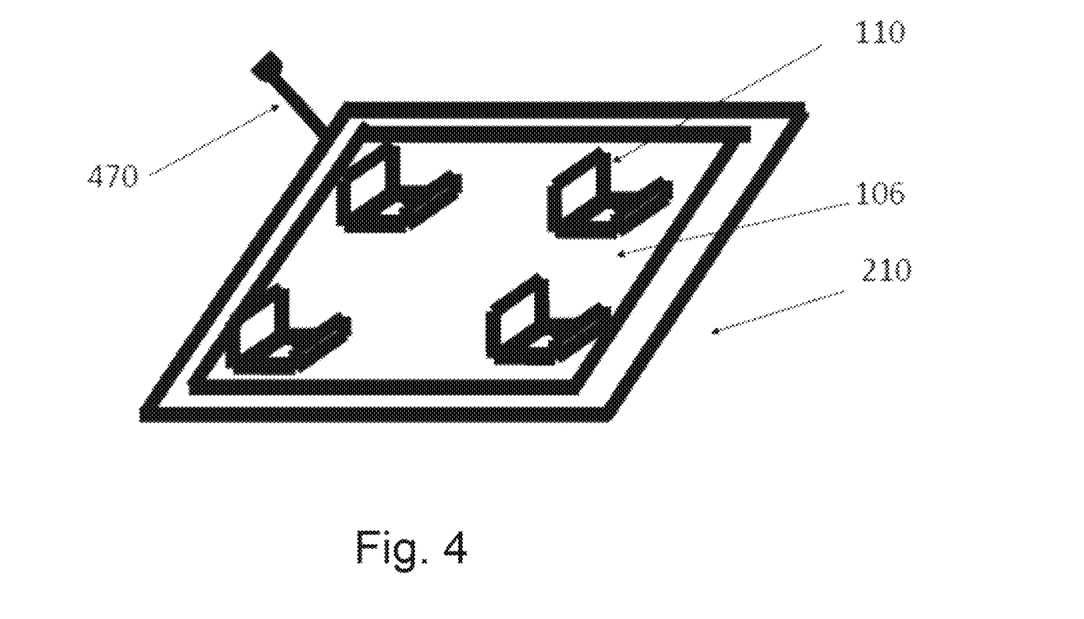
FIG. 4 shows the cabinet draw insert with tablet cradles.
Figure 5:
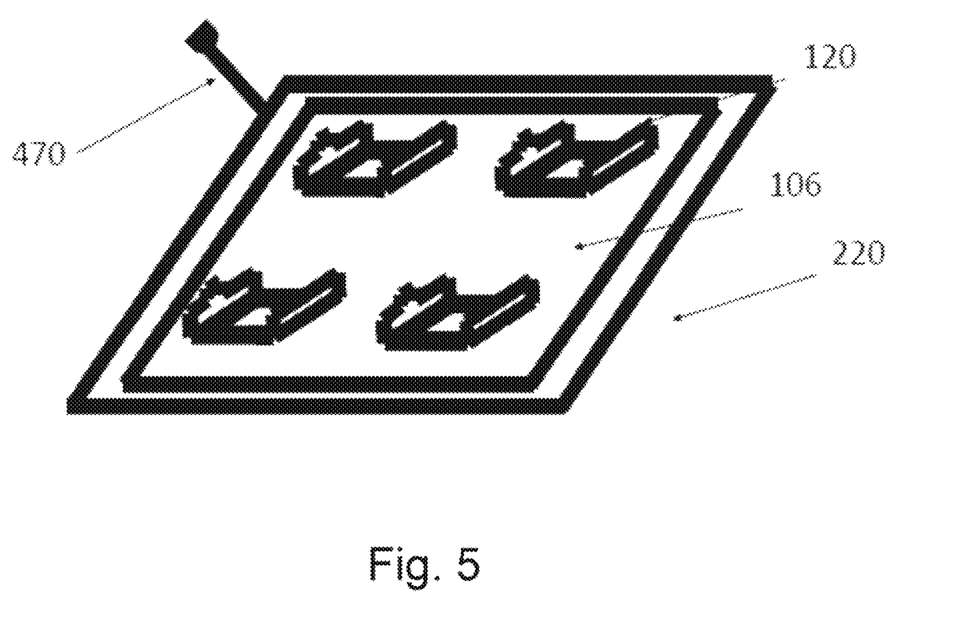
FIG. 5 shows the cabinet draw insert with headset cradles.

The preferred embodiment of the kit of the invention the kit contains the following components: as shown in FIG. 4 the cabinet draw insert 210 with tablet cradles 110 for storing tablets, as shown in FIG. 5 the cabinet draw insert 220 with headset cradles 120 for storing headsets. As shown in FIG. 6 the brushes 405, ultraviolet light modules 410 having ultraviolet lights 399, power supply 710, wiring harness for ultraviolet light modules 420, fan 425, electronic controller 430 for the sterilization process with the UV lights, timer 440, indicator light 450 for indicating that the UV light sterilizing process is in operation, audible alert 460 or indicating that the UV sterilization process is complete.

A next most preferred embodiment of the kit of the invention the kit contains the following components: cabinet draw insert 220 with headset cradles 120 for storing headsets, brushes 405, ultraviolet light modules 410 having ultraviolet lights 399, power supply 710, wiring harness for ultraviolet light modules 420, fan 425, electronic controller 430 for the sterilization process with the UV lights, timer 440, indicator light 450 for indicating that the UV light sterilizing process is in operation and for indicating that the UV sterilization process is complete.

Figure 12:
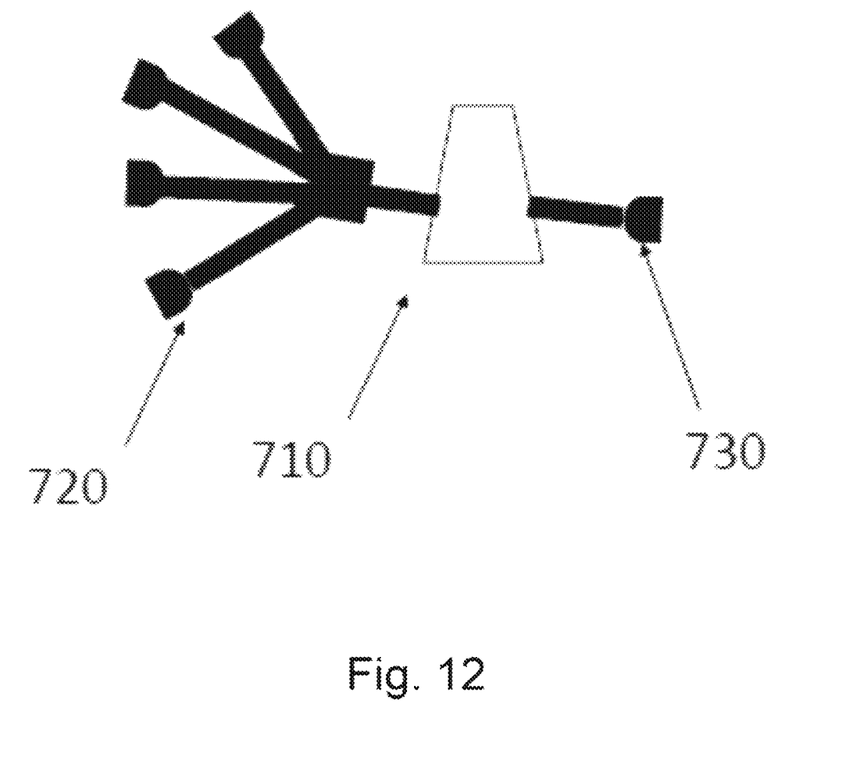
FIG. 12 shows the power supply of the invention.

The cabinet draw inserts 210 and 220 have wiring harness 470 that is connected to wiring harness 720 on the power supply 710 as shown in FIG. 12. The power supply 710 wiring harness 730 is adapted to be compatible with the wiring of the tablet storage cart 100. Each kit will contain the number of cabinet draw insert 210 with tablet cradles 110 and cabinet draw insert 220 with headset cradles 120 requested by the user. A key difference between the prior art and the current embodiments is the cabinet draw inserts 210 and 220 are open on the bottom or have a clear plastic 106 such as plexiglass, PETG or acrylic floor to permit the UV sterilization process to address all sides of the tablets and headsets.

Each kit is configurable and will contain the number of cabinet draw insert 210 with tablet cradles 110 requested by the user.

Each kit is configurable and will contain the number of cabinet draw insert 220 with headset cradles 120 requested by the user.

The ultraviolet light modules 410 having ultraviolet lights 399 are designed to illuminate the cabinet draw insert 210 with tablet cradles 110 and cabinet draw insert 220 headset cradles 120 such that when a tablet is paced in the tablet cradles 110 and a headset is placed in a headset cradles 120 that the headset and tablet are exposed to a sufficient amount and intensity of UV light. The system also integrates a brush 405 which is placed on the rear wall of each cabinet draw insert 210 and 220 which brushes the dust off of the UV light modules each time a cabinet draw is open and closed therefore ensuring that the UV lights are operating a maximum efficiency. UV lights are susceptible to degradation due to obstruction from dust and other materials which obstruct the light so insuring that they are clean is an important feature of the invention and the brushes 405 ensure that the lights are cleaned prior to and after a cleaning session. The ultraviolet light modules 410 having ultraviolet lights 399 with wiring harness and connector 411 can be selected from either UV light sources such as Mercury-based lamps s or LED's and also need the required power supply 710 to provide adequate voltage and amperage to the lights. Connector 411 attaches to connector 720 on power supply 710.

Figure 8:
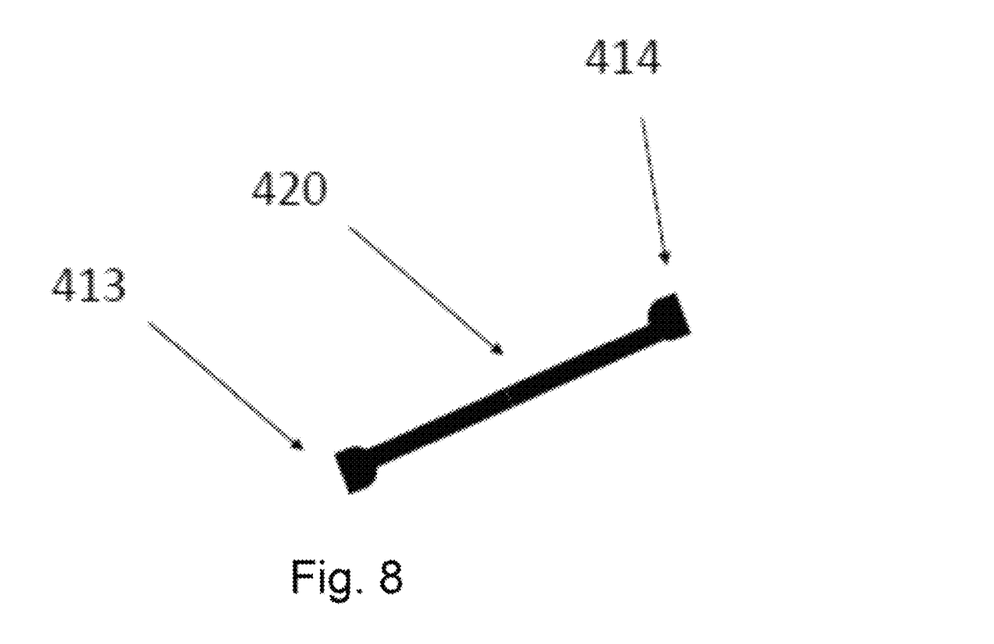
FIG. 8 shows the wiring harness for ultraviolet light modules.
Figure 10:
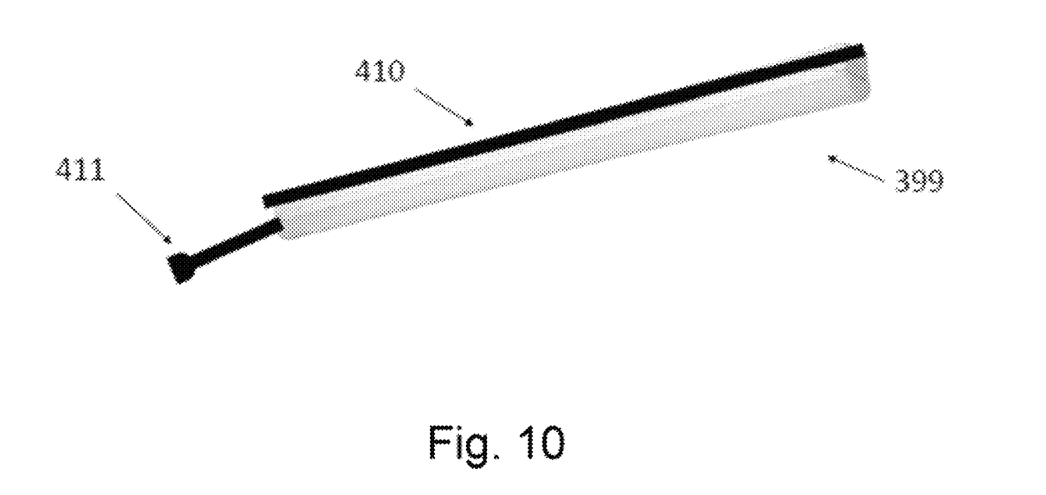
FIG. 10 shows a schematic of a UV light module.
Figure 11:
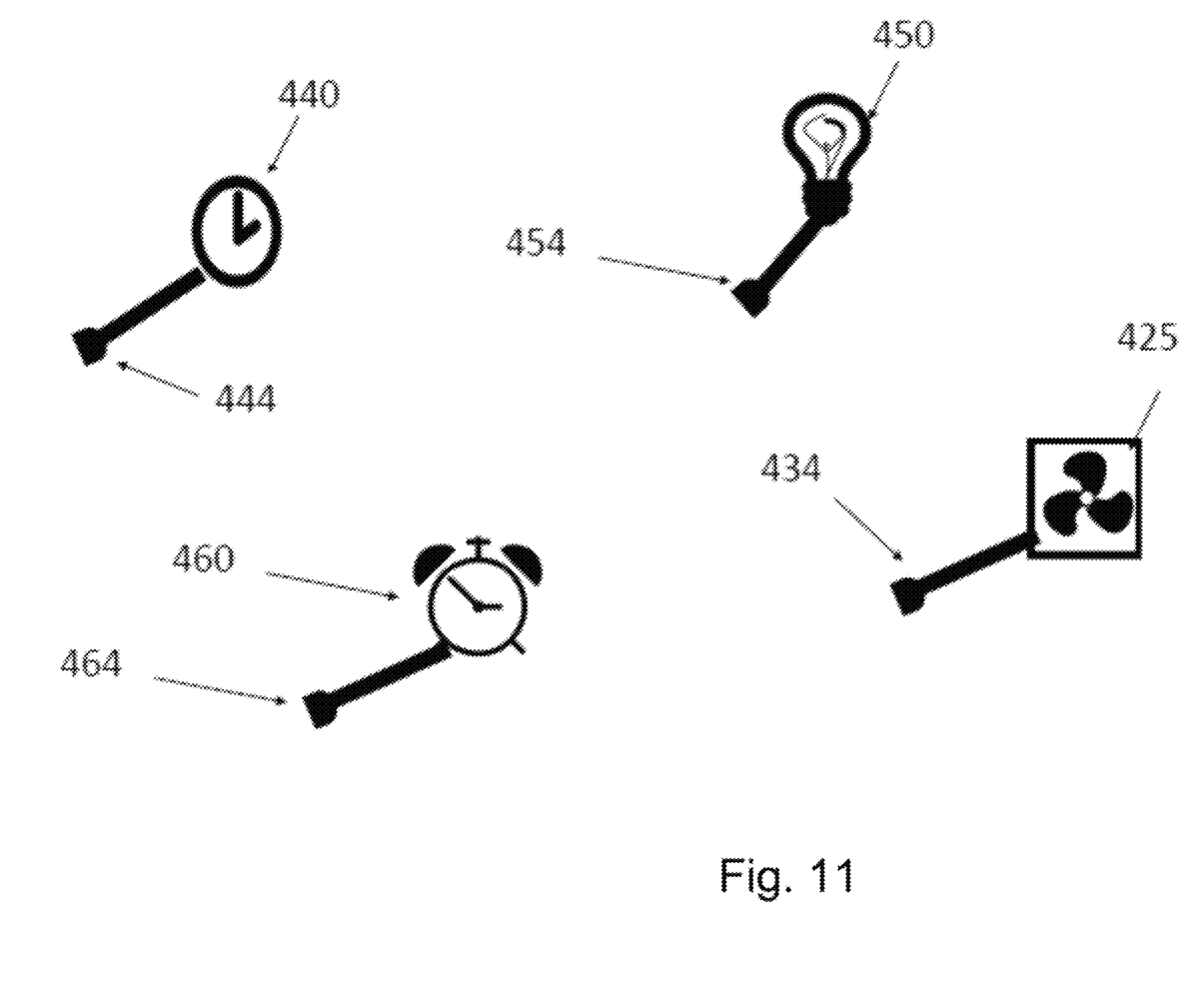
FIG. 11 shows the schematic of a fan module, timer module, indicator light module and audible alarm module.

The wiring harness 420 shown in FIG. 8 and FIG. 10 for ultraviolet light modules 410 is configured with the proper number of connectors 411 to receive the receptacles 720 from the power supply 710 as shown in FIG. 10. The connector 730 is compatible with the wiring of electronic controller 430 input connectors 412 on electronic controller 430.

Figure 9:
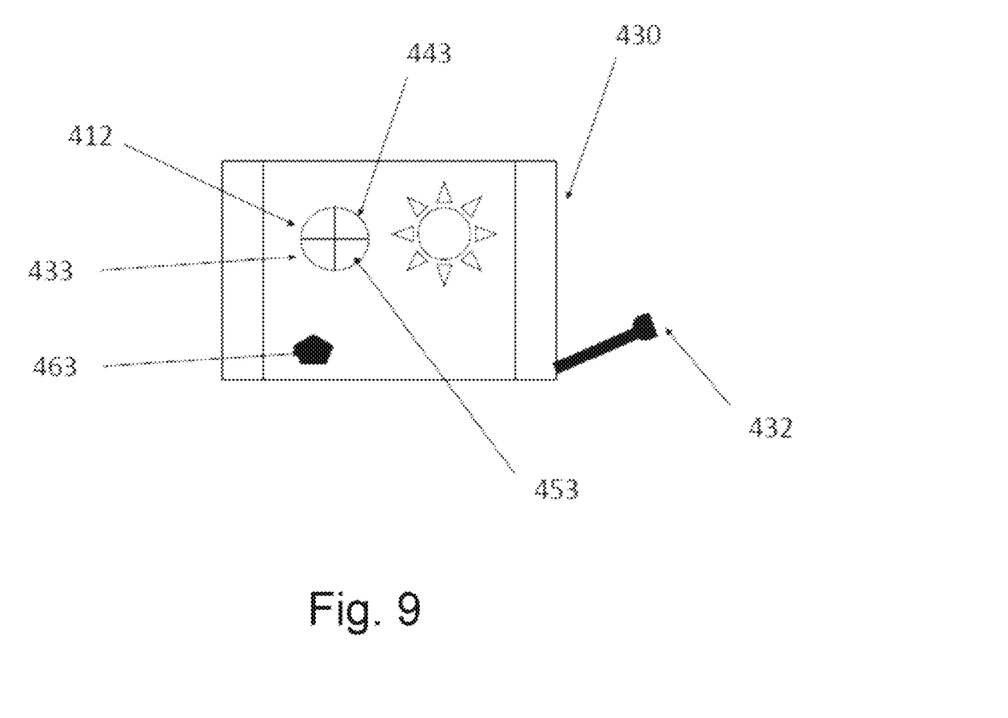
FIG. 9 shows a schematic of an electronic controller.

Referring to FIG. 9 the electronic controller 430 is configured with a power connector which is compatible with the wiring harness tablet storage cart 100 and connects to it using receptacle 432.

The fan 425 is configured with a power connector 434 which is compatible with the fan output receptacle 433 on the electronic controller 430. The fan is designed to move the air throughout the cabinet to ensure that the UV sterilization baths all the tablets and headsets.

The timer 440 is configured with a power connector 444 which is compatible with the fan output receptacle 443 on the electronic controller 430.

The indicator light 450 is configured with a power connector 454 which is compatible with the fan output receptacle 453 on the electronic controller 430.

The audible alert 460 is configured with a power connector 464 which is compatible with the fan output receptacle 463 on the electronic controller 430.

Figure 7:
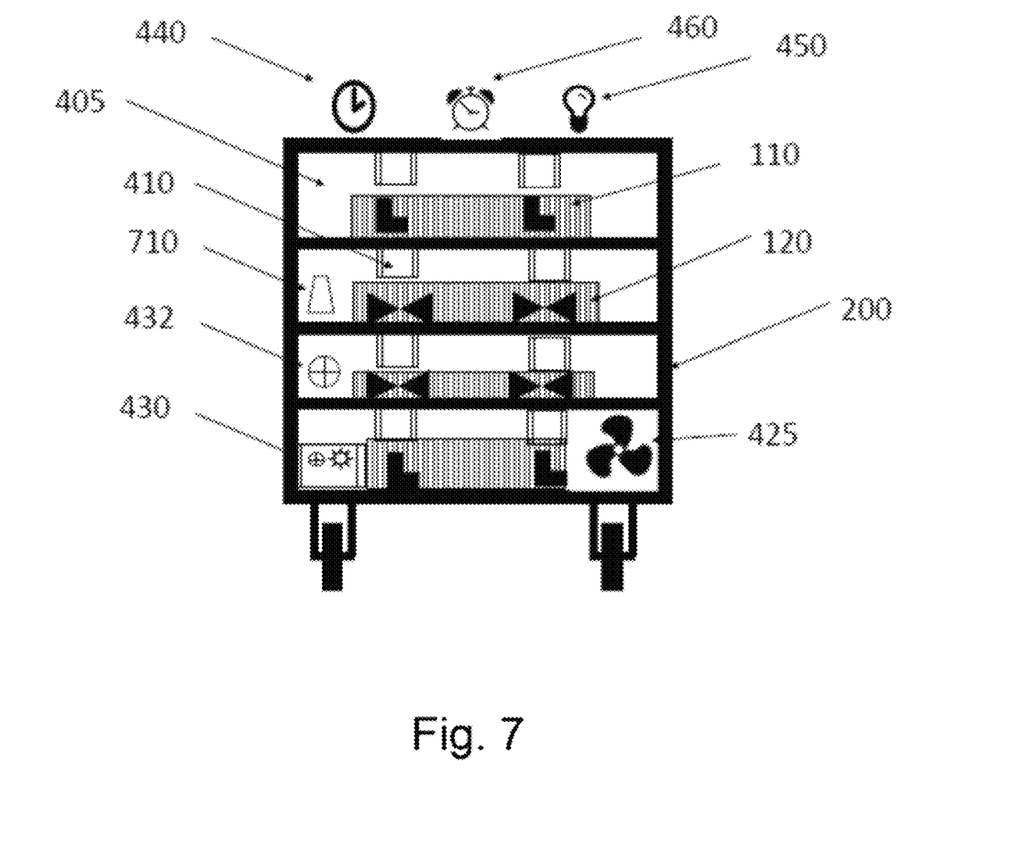
FIG. 7 shows the front view of the tablet and headset storage cart after conversion.

As shown in FIG. 7 the process of utilizing the kit of the preferred embodiment involves the user removing the tablet storage cart 100 draws 105 with tablet cradles 110 and headset cradles 120 for storing the tablets and the headsets and replacing the tablet cradles 110 and headset cradles 120 with the cabinet draw insert 210 with tablet cradles 110 and cabinet draw insert 220 headset cradles 120. The cabinet draw inserts 210 and 220 must be positioned in the tablet storage cart 100 draws 105 such that the open bottom or have a clear plastic bottom 106 such as plexiglass, PETG or acrylic floor is will be facing the draw or floor below of the tablet storage cart 100 to permit the UV sterilization process to address all sides of the tablets and headsets when the draws 105 is replaced in the tablet storage cart 100.

Next the user installs a brush 405 is positioned on the rear of each cabinet draw insert 210 with tablet cradles 110 and cabinet draw insert 220 headset cradles 120 and secured to the back of the cabinet draw insert 210 and cabinet draw insert 220 so that when the draws 105 is installed in the tablet storage cart 100 that the brushes will clean the UV light modules 410 having ultraviolet lights 399 when they are installed on the draws 105 with tablet cradles 110. The brush 405 can be installed using either screws, Velcro, adhesive or any other type of fastening method applicable. The material for the brush 405 can be selected from synthetic bristles on brushes or natural bristles. These are usually made out of nylon, polyester or a combination of these materials' animal hair such as pig, horse, and squirrel fur.

Next the ultraviolet light modules 410 are attached to the bottom of the draws 105 or cabinet draw insert 210 and cabinet draw insert 220 depending on the configuration of the tablet storage cart 100. The ultraviolet light modules 410 can be installed using either screws, Velcro, adhesive or any other type of fastening method applicable. The ultraviolet light modules 410 having ultraviolet lights 399 with wiring harness and connector 411 and are connected to the power supply 710 to provide adequate voltage and amperage to the lights. Connector 411 attaches to connector 720 on power supply 710.

The wiring harness 420 shown in FIG. 8 and FIG. 10 for ultraviolet light modules 410 is configured with the proper number of connectors 411 to receive the receptacles 720 from the power supply 710 as shown in FIG. 10.

The connector 730 is compatible with the wiring of electronic controller 430 input connectors 412 on electronic controller 430.

Next the user installs the fan 425 in the tablet storage cart 100 by attaching it inside of the cabinet of the tablet storage cart 100. The fan 425 can be installed using either screws, Velcro, adhesive or any other type of fastening method applicable.

Next the user installs the electronic controller 430 for the sterilization process with the power supply and UV lights in the tablet storage cart 100 by attaching it inside of the cabinet of the tablet storage cart 100. The electronic controller 430 can be installed using either screws, Velcro, adhesive or any other type of fastening method applicable.

Next the user installs the timer 440 by attaching it inside of the cabinet of the tablet storage cart 100. The timer 440 can be installed using either screws, Velcro, adhesive or any other type of fastening method applicable.

Next the user installs the indicator light 450 for indicating that the UV light sterilizing process is in operation and the audible alert 460 or indicating that the UV sterilization process is complete to the tablet storage cart 100. The indicator light 450 and the audible alert 460 can be installed using either screws, Velcro, adhesive or any other type of fastening method applicable.

Next the user installs the draws 105 with cabinet draw insert 220 with headset cradles 120 and cabinet draw insert 210 and cabinet draw insert 220 into the tablet storage cart 100 and connects all the ultraviolet light modules 420 using the wiring harness for ultraviolet light modules 420 to the electronic controller 430.

Next the user connects the fan 425, timer 440 and indicator light 450 to the electronic controller 430 using the appropriate connectors and wires.

The user can then test the system by placing tablets and headsets into the appropriate table. Setting the timer 440 to the appropriate time to ensure adequate sterilization and the electronic controller 430 turns on the fan 425 and the indicator light 450. The electronic controller 430 turns t of when the timer he audible alert 460 on, the fan 425 and the indicator light 450 when the timer 440 expires.

The process of utilizing the kit of the next most preferred embodiment involves the user removing the tablet storage cart 100 draws 105 with tablet cradles 110 for storing the tablets and replacing the tablet cradles 110 with the cabinet draw insert 220 headset cradles 120. The cabinet draw inserts 220 must be positioned in the tablet storage cart 100 draws 105 such that the open bottom or have a clear plastic bottom 106 such as plexiglass, PETG or acrylic floor is will be facing the draw or floor below of the tablet storage cart 100 to permit the UV sterilization process to address all sides of headsets when the draws 105 is replaced in the tablet storage cart 100.

The kit installation is then the same process as that used in the most preferred embodiment.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A kit for the conversion of an existing tablet charging storage cart to a tablet and virtual reality headset charging and sterilization storage cart and said tablet charging storage cart having at least a first cabinet draw having a first cabinet draw insert and said tablet charging storage cart having at least a second cabinet draw and said second cabinet draw having a second cabinet draw and wherein said kit comprising:
    a. at least one cabinet draw insert with tablet cradles;
    b. at least one cabinet draw insert with headset cradles; at least one brush for cleaning ultraviolet lights;
    c. at least one ultraviolet light module having an ultraviolet light;
    d. at least one power supply;
    e. a wiring harness for ultraviolet light modules;
    f. a fan;
    g. an electronic controller;
    h. a timer;
    i. an indicator light;
    j. an audible alert,
        said at least one cabinet draw insert with tablet cradles replaces said existing said first tablet charging storage cart draw insert, said at least one cabinet draw insert with headset cradles replaces said existing said second tablet charging storage cart draw insert.

2. The kit of claim 1 wherein said cabinet draw insert with tablet cradles having a clear plastic floor and a rear wall and said brush attached to said rear wall for cleaning said ultraviolet lights.

3. The kit of claim 2 wherein said clear plastic floor is selected from the group consisting of plexiglass, PETG and acrylic.

4. The kit of claim 1 wherein said cabinet draw insert with headset cradles having a clear plastic floor and a rear wall and said brush attached to said rear wall for cleaning said ultraviolet lights.

5. The kit of claim 4 wherein said clear plastic floor is selected from the group consisting of plexiglass, PETG and acrylic.

6. The kit of claim 1 wherein said ultraviolet light is selected from the group consisting of Mercury-based lamps, Ultraviolet light-emitting diodes and Pulsed-xenon lamps.

7. The kit of claim 6 wherein said Mercury-based lamps operating wavelength is 253.7.

8. The kit of claim 6 wherein said Ultraviolet light-emitting diodes operating wavelength is between 255 and 280 nm.

9. The kit of claim 6 wherein said Pulsed-xenon lamps operating wavelength has a peak emission near 230 nm.

10. The kit of claim 1 where said brush has bristles and said bristles are selected from the group consisting of nylon, polyester, polyester and nylon blend, pig hair, horsehair, and squirrel fur.

\* \* \* \* \*